United States Patent
Pedersen et al.

(10) Patent No.: US 6,468,521 B1
(45) Date of Patent: Oct. 22, 2002

(54) STABILIZED COMPOSITIONS HAVING ANTIBACTERIAL ACTIVITY

(75) Inventors: Lars Haastrup Pedersen, Gistrup (DK); Peter Boman Samuelsen, Rungsted Kyst (DK); Kim Lambertsen Larsen, Aalborg Oist (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/774,180

(22) PCT Filed: Aug. 13, 1999

(86) PCT No.: PCT/DK99/00434
§ 371 (c)(1), (2), (4) Date: Feb. 1, 2001

(87) PCT Pub. No.: WO00/09173
PCT Pub. Date: Feb. 24, 2000

(30) Foreign Application Priority Data

Aug. 14, 1998 (DK) ......................................... 1998 01033

(51) Int. Cl.$^7$ .......................... A61K 47/48; A61F 13/00; A61F 2/00
(52) U.S. Cl. ...................... 424/78.17; 424/422; 424/423
(58) Field of Search .............................. 424/78.17, 406, 424/422, 423

(56) References Cited

U.S. PATENT DOCUMENTS

| | | | |
|---|---|---|---|
| 3,911,115 A | 10/1975 | Hadhanyl | 424/180 |
| 5,326,567 A | 7/1994 | Capelli | 424/405 |
| 5,429,819 A | 7/1995 | Oka et al. | 424/400 |
| 5,869,073 A * | 2/1999 | Sawan et al. | 424/406 |

FOREIGN PATENT DOCUMENTS

| | | |
|---|---|---|
| DE | 2 260 536 | 7/1974 |
| EP | 0 272 149 | 6/1988 |
| EP | 0 591 440 | 4/1994 |
| EP | 0 596 615 | 5/1994 |
| GB | 591440 | 8/1947 |
| JP | 8245325 | 9/1996 |

OTHER PUBLICATIONS

WPI, Derwent accession No. 1988–178826, abstract (JP 63 115 566).*
WPI, Derwent accession No. 1996–482068, bastract (JP 08 245 325).*
WPI, Derwent accession No. 1988–178826; Nippon Zeon KK; Wound–covering material preventing exudation, etc. —Comprises . . .

* cited by examiner

Primary Examiner—Thurman K. Page
Assistant Examiner—Blessing Fubara
(74) Attorney, Agent, or Firm—Jacobson Holman, PLLC

(57) ABSTRACT

A stabilised composition having antibacterial, antiviral and/or antifungal activity characterised in that it comprises a silver compound and that the compound is in the form of a complex with a primary, secondary or tertiary amine which complex is associated to one or more hydrophilic polymers is stable during sterilisation and retaining the activity without giving rise to darkening or discoloration of the dressing during storage.

8 Claims, No Drawings

STABILIZED COMPOSITIONS HAVING ANTIBACTERIAL ACTIVITY

FIELD OF THE INVENTION

The present invention relates to stabilised compositions having antibacterial, anti-viral and/or antifungal activity, to a method of producing such compositions, medical devices having a coating comprising such compositions, and the use of the stabilised compositions for producing a wound dressing, an ostomy appliance, an incontinence device, other medical devices or hydrophilic coatings.

BACKGROUND OF THE INVENTION

The antiseptic activity of silver compounds is a well known property which has been utilised for many years. The bacteriostatic and fungistatic effect is caused by the silver ion and a simple compound which has been used clinically is for instance silver nitrate. Silver nitrate in concentrations of 0.5–1% in water shows disinfectant properties and is used for preventing infections in burns or for prophylaxis of neonatal conjunctivitis. For another silver compound, silver sulfadiazine, the antibacterial effect of the sulfadiazine molecule is further enhanced by the complexing with the disinfecting silver ion. In contrast to the silver nitrate, the solubility of the silver sulfadiazine complex is low and hence, both of the two active parts are only present in solution in low concentrations but may be present over a longer period of time before being washed out at site to be treated. The silver sulfadiazine is intensively used in the treatment of wounds, in particular bums, under the trademarks Silvadene® and Flamazine®. Silver-protein-combinations are yet other antiseptic formulations which have been used in low concentrations as eye drops.

Bacteriostatics based on the silver ion are further used in various medical devices. One example of such application is the use in the wound dressing sold by Johnson & Johnson under the trademark Actisorb® which is an activated charcoal cloth dressing. Another example is the wound dressing sold under the trademark EZ-Derm by Genetic Laboratories which dressing is a modified pigskin impregnated with a soluble silver compound intended for treatment of burns. A number of patents discloses compositions or devices showing antiseptic properties based on contents of silver compounds. EP 272 149 B1 discloses a medical dressing of the 'hydrocolloid' type containing and releasing active components. Silver chloride is a specific antiseptically acting compound mentioned in this patent.

A specific advantage in using the silver ion as bacteriostatic agent is the general lack of formation of bacterial tolerance to the compound. This is in contrast to many types of antibiotics. However a major drawback when using ionic silver for bacteriostatic purposes is the reduction of the ion to free silver which results in dark stainings. Such staining has been reported to give potentially permanent pigmentation of the skin, the so-called argyria. It is commonly recognised that silver containing compounds will discolour by influence of light and or heat, and it will often be found that sterilisation by radiation may lead to a unsatisfactory change of the colour of a composition in which it is comprised, irrespective of the use in a solution, cream or gel or a medical device. Furthermore, such antibacterial compositions are often intended used in connection with medical or cosmetic products under circumstances where a discoloration is very unfortunate and potentially precluding for the use.

Recently, principles of antimicrobial metal-based compositions being photo stable, have been disclosed in U.S. Pat. No. 5,326,567 to Capelli and in U.S. Pat. No. 5,429,819 to Oka. In U.S. Pat. No. 5,326,567 a 'host-guest' relationship between silver ions and acyclic polyethers is accomplished through the use of excess of halide ions. In U.S. Pat. No. 5,429,819 is disclosed a photo-stable composition comprising a complex of the silver ion with a thiosulphate salt carried on a porous particulate carrier. In U.S. Pat. No. 3,911,115 (DE patent No. 22 60 536) a cycloheptaamylose (β-cyclodextrin) alkanol amine compound is claimed to posses stabilisirc effects on silver. However, in praxis the cycloheptaamylcse alkanol amine complex is not effective in preventing discolouring and furthermore, for medical purposes it is disadvantageous to introduce an alkanol giving rise to formation of a toxic carrier complex for the silver as the alkanolamines generally are known as irritants and moderate toxic compounds having numerous potential side effects (Patty's Industrial Hygiene and Toxicology, Vol. II, Part B, 4th ed. 1994).

It is commonly recognised that compounds containing silver will discolourise in presence of light and or heat, as well as it often will be found that radiation sterilisation process will lead to a dissatisfactory change of colour of the composition in which it is comprised whether it is in a cream or a gel or a medical device. Moreover, such antibacterial compositions are often intended for use for medical or cosmetic purposes under which circumstances a discoloration is very unfortunate and potentially prevents the use of silver ions for said use.

None of the above references describe examples of hydrophilic polymer formulations or devices comprising such formulations containing silver compounds for use as antiseptic being stable against discoloration due to reduction of the silver ion or being stable against potential convertion of the silver ion into the dark stained compounds of silver such as metallic silver or the silver sulphide.

It is an object of the present invention to provide complex structure rendering silver ions stable against loss of the antiseptic activity and against darkening due to reduction of the silver ions or the formation of darkly stained sparingly or insoluble silver compounds.

Further it is an object of the invention to provide principles and methods of introducing the silver compositions stabilised against the effect of light into catheters guidewires or similar medical devices or instruments.

It has now surprisingly been found that silver ions may effectively be stabilised against exposure to light by formation of simple complexes with primary, secondary or tertiary amines which complexes are associated to hydrophilic polymers.

BRIEF DESCRIPTION OF THE INVENTION

The present invention relates to stabilised compositions having antibacterial, antiviral and/or antifungal activity.

Furthermore, the invention relates to a method of producing compositions having antibacterial, antiviral and/or antifungal activity.

Still further, the invention relates to medical devices having a coating comprising compositions having antibacterial, antiviral and/or antifungal activity.

The invention also relates to the use of the stabilised compositions having antibacterial, antiviral and/or antifungal activity for producing a wound dressing or an ostomy appliance, an incontinence device, other medical devices or hydophilic coatings.

DETAILED DESCRIPTION OF THE INVENTION

The present invention relates to a stabilised composition having antibacterial, arinivral and/or antifungal activity which composition is characterised in that it comprises a silver compound in the form of a complex with a primary, secondary or tertiary amine which complex is associated to one or more hydrophilic polymers.

The amine being used in the compositions of the invention are suitably a primary, secondary or tertiary lower alkyl amine or amino alcohol having a free lone pair of electrons.

A lower alkyl amine is preferably selected from mono, di or tri methyl, ethyl, propyl or butyl amines or mixtures thereof.

A lower alkyl amino alcohol is preferably selected from mono, di or tri methyl ethyl or propyl aminoalcohols or mixtures thereof.

The compositions of the present invention will show alkaline properties in aqueous solutions and the pH may be adjusted to a value from 6.5 to 8.5 or/or neutralised using an appropriate acid such as a mineral acid such as hydrochloric acid.

Without restricting the invention to any specific theory, it is believed that the stabilisation of the silver compound is to be ascribed to a formation of a complex between the silver ion and the amines offering a free lone pair of electrons for complexation. Surprisingly this type of silver complexes have been shown to be stable not only in dry conditions but also in aqueous solutions containing ionic polymers such as various types of derivatized polysaccharides which are often used in hydrogels or other types of wound dressings. Furthermore, medical devices such as catheters, stents or guide wires often contain the antibacterial substance in a hydrophilic coating which may otherwise destabilise the silver under processing or storage if it is not in a stabilised form.

Thus, it is assumed that silver salts may be stabilised in solution by amines in which the nitrogen atom has an active free lone pair of electrons. For the purpose of the present invention the term "stabilisation" is intended to cover an improvement of the stability of the silver ion against the influence light and heat which normally leads to formation of dark stained free silver.

It is known that solutions of silver salts may fairly easily be stabilised against heat and light when stabilised with dextrines and thiosulfates. These types of complexes has, however, shown not to be stable in presence of hydrophilic polymers especially the strongly polar or ionic polymers. The stabilisation of silver with the amines according to the present invention also provides stability in the presence of such polymers. As ionic and polar polymers are used increasingly in medical devices and as silver compounds are effective antibacterial agents combinations of these are very desirable. The present invention offers the option of using such combinations without risking discoloration as well as methods of producing compositions comprising and medical devices comprising the same.

None of the above references teach the complexation between silver compounds and primary, secondary or tertiary and moreover do not teach the stabilisation of complexes associated to hydrophilic polymers against discoloration.

The hydrophilic polymers used in the compositions according to the invention are suitably selected from synthetic hydrophilic polymers and derivatives of animal or vegetable hydrophilic polymers. In a preferred embodiment of the invention the hydrophilic polymer is selected from the polysaccharides. Polysaccharides to be used according to the invention are preferably cellulose derivatives. Preferred cellulose derivatives are sodium carboxymethylcellulose and hydroxyethylcellulose.

In another embodiment of the invention the hydrophilic polymer is selected from the alginates. An alginate is preferably the sodium alginate.

In yet another embodiment of the invention the hydrophilic polymer is selected from collagens. Preferably porcine collagen is used.

In yet further embodiments of the invention the hydrophilic polymer is selected from glucosaminoglycans and proteoglycans.

In still another, preferred embodiment the composition according to the invention is a hydrophilic polymer which forms a gel or xerogel.

The polymers to be used in the compositions of the present invention may be in the form of a polymer forming a network of crosslinked or non crosslinked hydrophilic polymer.

Preferably the hydrophilic polymer is a polysaccharide and preferably from the group of the cellulosic derivatives having various substituents. Such polymers are readily available from the nature or from synthetic modification. Other preferred polymers are polylactic acid, polyhydroxybutyrates or similar polyesters, polyvinyl alcohol, poiyvinylporrolidone, polyacrylates, hydrophilic polyurethanes, polymaleic acid and polymers of natural origin like glucosaminoglycans, collagen and fibrin or the like as well as copolymers or derivatives thereof.

Further, such polymers may be crosslinked into three dimentional networks.

Silver salts to be used according to the invention may be readily soluble salts like the nitrate, lactate, or acetate or more heavily soluble salts like the halogenides such as the chloride or bromide. The silver salt is preferably silver nitrate, silver acetate or silver lactate. Thus, the choice of silver compound for the purpose of the present invention is not critical.

The concentration of silver in the composition according to the invention is preferably from 0.1 to 30% by weight of the dry matter, more preferred from 0.5 to 5% by weight of the dry matter.

The compositions of the invention may be e.g. used in wound dressings. In particular the material is suitable for incorporation in traditional gauzes and compresses, hydrocolloid dressings or xerogel dressings. In such dressings the silver composition according to the invention is readily incorporated by dissolution in water and impregnation into dressings like gauze, or they may be introduced as a component of said dressing, e.g. a component of an adhesive composition, by a manner known per se. A method for incorporation in hydrocolloid dressings is disclosed in GB Patent 591,440, Samuelsen et al. A method for incorporation of the composition in alginate fibre dressings or similar dressings is by simply adding the composition to the solution comprising the alginate before this is further processed into a fibrous material. Introduction may also take place in the form of a powder which is easily obtained for instance by grinding a lyophilised or spray-dried material. In wound dressings the compound may be introduced into the adhesive for fixing the dressing to the wound site or into another part of the dressing, for instance a foam pad.

The compositions of the invention and formulations thereof may be used for antibacterial, antiviral or antifungal use in the area of human or veterinary medicine. Such formulations may be in the form of a cream or gel intended for dermatological use on skin, in wounds or other body cavities. Formulations may also be in form of powders for similar purposes or for skin folds or athletes foot or the like in the veterinary area.

The antibacterial property may not be the intended and most important property of such formulations but an concomitant property.

Many other types of products are suitable for incorporation of the silver compositions of the invention for instance foam or other vaginal inserts for use in the continence care, condoms, male external urine catheters, skin adhesives etc. Furthermore, the compositions may be used in products not necessarily being in direct contact with the body such as powders for removal of odour in incontinence pads or for incorporation into ostomy pouches.

The silver compositions of the invention may also be used in implants and sutures or materials that for a period will be left in body cavities. This will be advantageous in connection with surgery where the risk of infection is always latent. Systemic prophylactic treatment with antibiotics in combination with a proper antiseptic treatment of the skin are in most cases common practice. Often medical articles that are implanted or for other reasons left in a surgical opening are carrying antiseptics or even antibiotics. The present invention offers an advantageous alternative to known compositions comprising silver as the composition of the invention has broad antiseptic properties and secures stability during storing and in use. Moreover it is very suitable for controlled release for instance when incorporated in polylactic acid for sutures or implants or when incorporated in implants based on hydroxyl apatite. Furthermore, the silver compositions of the invention are suitable for incorporation into haemostats based on e.g. alginate fibre or foam dressings as well as materials based on collagen or gelatine. Still further, the compositions may be introduced into gel-like materials intended to be protecting covers for e.g. anastomoses formed in bowel or vascular surgery.

The invention also relates to a medical device comprising an impregnation or coating comprising a silver compound in the form of a complex with a primary, secondary or tertiary amine which complex is associated to one or more hydrophilic polymers.

Furthermore, the invention relates to a method of producing compositions having antibacterial, antiviral and/or antifungal activity in which a silver salt is dissolved in water, an amine is added and the resulting solution is left for a period of from 2 to 100 hours, optionally after adjusting the pH using an acid, the resulting mixture is added to a hydrophilic polymer and optionally dried and micronised.

Still further, the invention relates to the use of stabilised compositions comprising a silver compound in the form of a complex with a primary, secondary or tertiary amine which complex is associated to one or more hydrophilic polymers, said composition having antibacterial, antiviral and/or antifungal activity for producing a wound dressing, an ostomy appliance, an incontinence device, other medical devices or hydrophilic coatings.

The invention is explained more in detail in the working examples below disclosing embodiments and properties of compositions of the invention. It is evident that many variations may be made without diverging from the invention the scope of which is set forth in the appended claims.

MATERIALS AND METHODS

EXAMPLE A

Preparation of a Stock Solution of Silver Nitrate

A stock solution of sliver nitrate was prepared by dissolving silver nitrate in distilled water to a concentration of 1.5 molar.

EXPERIMENTAL PART

REFERENCE EXAMPLE 1

Preparation of a Silver Compound as Disclosed in DE patent 22 60 536 and a Composition Comprising the Same 51 grams of beta-cyclodextrin was dissolved in 100 ml ethanolamine under stirring at 80° C. The solution was cooled to 35° C. in an ice bath. 10 grams of silver nitrate was added under stirring until a clear solution was obtained. Further 205 ml of warm ethanolamine having a temperature of 35° C. was slowly added whereafter the solution is filtered through a Whatman No. 1 filter. The resulting solution was cooled to 5° C. for precipitation over 24 hours. The precipitate was filtered from the residual ethanolamine and washed with cold acetone (7 times 80 ml) until no more silver can be detected in the washing liquid.

A gel of sodium-carboxymethylcellulose containing the complex as above was produced from 100 ml distilled water, 4 g sodium-CMC and 0.67 g of the purified complex obtained above in an analogous manner as described in Example 1. The resulting composition contained 1% silver, based on dry weight.

REFERENCE EXAMPLE 2

Preparation of a CMC Gel Comprising Silver Nitrate

A gel composed of 4% sodium carboxyl cellulose was produced by adding the polymer in an amount of 4 g/100 ml to a silver nitrate solution of a concentration of 0.068% by simple dissolving at ambient temperature using a stirrer over 8 hrs.

EXAMPLE 1

Preparation of a Stabilised Silver Compound According to the Invention

To 0.5 ml of the 1.5 molar solution was added 3.7 ml of 1.8 molar tri-hydroxymethyl-aminomethane titrated to pH 6.9 using 1.0 N hydrochloric acid.

The silver-amino complex was equilibrated for 72 hours at ambient temperature in the dark.

Finally, 200 ml distilled water and 8 g sodium-carboxymethyl-cellulose were added to the complex.

The resulting composition contained 0,036 molar silver complex in a 3.9% Carboxymethylcellulose gel.

EXAMPLE 2

Preparation and Lyophilization of a Stabilised Silver Compound According to the Invention A composition prepared in the same manner as disclosed in Example 1 was lyophilised over night and micronized to a powder with average particle size of 20–50 micrometers, The resulting powder contains 0.95% silver.

EXAMPLE 3

Preparation of a Stabilised Silver Compound According to the Invention

To 0.5 ml of 1.5 molar solution of silver nitrate was added 2.9 ml of 1.8 molar trimethyl-aminomethane titrated to pH 7.5 with 1.0 N hydrochloric acid. The composition was allowed to stand for 72 hours in the dark at ambient temperature. To the resulting solution were added 200 ml distilled water and 4 grams of sodium-carboxymethylcellulose were added to the silver complex. The resulting composition contained 0.036 molar silver complex in 2.0% carboxymethylcellulose gel.

EXAMPLE 4

Preparation of a Stabilised Silver Compound According to the Invention

In the same manner as disclosed in Example 1 a stabilised silver compound was produced using sodium alginate instead of carboxymethylcellulose.

EXAMPLE 5

Preparation of a Stabilised Silver Compound According to the Invention Comprising Hydroxyethyl Cellulose Silver nitrate was dissolved in distilled water in a concentration of 1.0 molar. To 1 ml of the solution was added 2 ml of a 1.5 molar solution of ethylamine. The mixture was titrated to pH 8.0 with 1.0 molar hydrochloric acid and allowed to stand for 48 hours at ambient temperature in the dark.

To the composition was added 100 ml of a solution of 2.0% hydroxyethyl cellulose in destilled water.

The resulting composition contains 0.09 molar silver complex.

EXAMPLE 6

Preparation of a Stabilised Silver Compound According to the Invention

In the same manner as disclosed in Example 1 a stabilised silver compound was produced using porcine collagen instead of carboxymethylcellulose.

EXAMPLE 7

Comparison of Stability Against Discoloration of Compositions According to the Invention and of Known Compositions Stability against discoloration was determined in two ways as follows:

A: Stability to heat was determined by heating of the composition at 120° C. for 75 minutes for dry and gel compositions.

B: Stability to light was determined by exposure of sample to a light source tube (Osram L 58W/31-800) for 24 hours. Discoloration was determine spectrophotocally of a diluted gel sample in water (1:10) at a wave length of 425 nm using a Perkin Elmer UV/VIS spectrometer Lambda 2.

The results are summarized in the below Table 1 stating stability of compositions according to the invention prepared according to Examples 1–5 as compared to non stabilised compositions of Reference Examples 1–2.

TABLE 1

Stability against discoloration by UV light and heat

| Example | UV - discoloration index* | Heat - discoloration index** |
|---|---|---|
| 1 | 0.06 | Clear |
| 3 | 0.07 | Clear |
| 4 | 0.1 | Clear/yellowish |
| 5 | 0.55 | Yellowish |
| Reference 1 | 3.5 | Dark/brownish |
| Reference 2 | 10.5 | Dark |

*Index is calculated as (Abs(24 hrs) - Abs(0 hrs))/Abs(0 hrs)
**Subjective visual assessment

EXAMPLE 8

Preparation of a PVP-gel Comprising Silver Nitrate

To 91 ml of purified water at an ambient temperature was added 500 microliter 1.5M $AgNO_3$ and 3.75 ml of 2M TRIS (trihydroxymethyl aminomethane). The pH was adjusted to 7.5 by adding diluted nitric acid. Then 5 g of polyvinyl pyrrilidone (K-90 from ISP) was added under vigorous shaking. The mixture was then allowed to rest until all entrapped air has disappeared.

The resulting gel was sterilised with 3×11 kGy beta radiation, rendering a slightly yellowish and light stable gel.

What is claimed is:

1. A stabilised composition having antibacterial, antiviral and/or antifungal activity comprising a silver compound in the form of a complex with methyl, ethyl, propyl, or butyl amine or tri-hydroxymethylaminomethane which complex is associated to one or more hydrophilic polymers and wherein the hydrophilic polymers or a part thereof form a cross-linked three-dimensional network.

2. A composition as claimed in claim 1, wherein the composition has a pH from 6.5 to 8.5.

3. A composition as claimed in claim 1, wherein the hydrophilic polymer is selected from the group consisting of synthetic hydrophilic polymers, and polymers of natural origin.

4. A composition as claimed in claim 3, wherein the hydrophilic polymers form a gel or a xerogel.

5. A composition as claimed in claim 1, wherein the three-dimensional cross-linked hydrophilic polymer network comprises polyvinylpyrrolidone, polyvinyl ether, polyvinyl alcohol, polyurethanes, polyacrylates, polyacrylamides, collagen, gelatine, glucosaminoglucanes, modified polysaccharides, or a combination thereof.

6. A composition as claimed in claim 1, wherein the silver compound is silver nitrate, silver acetate, or silver lactate.

7. A composition as claimed in claim 6, wherein the concentration of silver is from 0.1 to 30% by weight of the dry matter.

8. A medical device having an impregnation or a coating comprising a silver compound in the form of a complex with a primary, secondary, or tertiary lower alkyl amine which complex is associated to one or more hydrophilic polymers.

* * * * *